United States Patent
Burk et al.

(10) Patent No.: US 6,414,187 B1
(45) Date of Patent: *Jul. 2, 2002

(54) ASYMMETRIC HYDROGENATION

(75) Inventors: Mark Joseph Burk, Cambridge (GB); Frank Bienewald, Versailles (FR); Antonio Zanotti-Gerosa, Cambridge (GB)

(73) Assignee: Chirotech Technology, Ltd. (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/673,119

(22) PCT Filed: Apr. 9, 1999

(86) PCT No.: PCT/GB99/01103
§ 371 (c)(1),
(2), (4) Date: Dec. 5, 2000

(87) PCT Pub. No.: WO99/52852
PCT Pub. Date: Oct. 21, 1999

(30) Foreign Application Priority Data

Apr. 9, 1998 (GB) .............................................. 9807888
Dec. 16, 1998 (WO) ............................... PCT/GB98/03784

(51) Int. Cl.$^7$ .............................................. C07C 57/50
(52) U.S. Cl. ...................................... 562/496; 562/512
(58) Field of Search ........................... 560/61, 81, 115, 560/127, 88, 122; 562/405, 433, 493, 496, 505, 507, 509, 512

(56) References Cited

U.S. PATENT DOCUMENTS 4,939,288 A    7/1990   Talley
5,728,866 A  * 3/1998   Rautebstrauch et al.
6,207,853 B1 * 3/2001   Burk et al.

FOREIGN PATENT DOCUMENTS

CH    WO-9600206 A1 *  1/1996
WO         9718894      5/1997

OTHER PUBLICATIONS

Organic Chemistry, Fifth Edition, T.W.G. Solomons, John Wiley & Sons, 1992 pp. 448–500.*

Yamamoto, Keiji et al. (1989) "Optimization of Asymmetric Hydrogenation of 3–phenyl–3–butenoic Acid Catalyzed by Rhodium(I)–4,5–bis'(diphenylphosphino)methyl'–2, 2–dimethyldioxolane (DIOP)" *Journal of Organometallic Chemistry* 370(1–3):319–332.

* cited by examiner

*Primary Examiner*—Gary Geist
*Assistant Examiner*—Paul Zucker
(74) *Attorney, Agent, or Firm*—Saliwanchik, Lloyd & Saliwanchik

(57) ABSTRACT

The present invention pertains to a process for the preparation of an enantiomerically enriched chiral carboxylic acid derivative having the partial formula: C—C—C—COOX wherein X is a cation, comprising formation of a dehydro precursor salt having the partial formula: C=C—C—COOX by reaction of the corresponding precursor acid with an at least substantially stoichiometric amount of base, and asymmetric hydrogenation of the salt in the presence of a transition metal complex of a chiral phosphine ligand.

22 Claims, No Drawings

ASYMMETRIC HYDROGENATION

FIELD OF THE INVENTION

This invention relates to processes suitable for the large scale preparation of enantiomerically enriched chiral carboxylic acid derivatives. In particular, it relates to asymmetric hydrogenation of prochiral substrates, using a transition metal catalyst complex.

BACKGROUND OF THE INVENTION

Asymmetric hydrogenation has been used to convert prochiral substrates having the partial formula C=C—C—COOX to chiral compounds of the formula C—C—C—COOX. See, for example, Yamamoto et al, *J. Organometallic Chem.*, 1989, 370, 319, where the substrate is 3-phenyl-3-butenoic acid, and the catalyst is Rh—DIOP. X depends on the additive, including tertiary amines.

Examples of other substrates in such a reaction have generally had a carboxylate function at at least one chiral centre. For example, itaconic acid derivatives have been used.

Enantiomerically enriched 2-substituted succinic acids (see formulae 2a and 2b, below) have recently attracted interest as useful chiral building blocks and pepidomimetics in the design of pharmaceuticals, flavours and fragrances, and agrochemicals with improved properties. For example, the utility of 2-substituted acid derivatives has been amply demonstrated through the synthesis of a range of new potent orally bioavailable drugs [J. T. Talley et al., in *Catalysis of Organic Reactions*, J. R. Kosak, T. A. Johnson (eds.) Marcel Dekker, Inc. (1994) Chapter 6; and H. Jendralla, *Synthesis* (1994) 494].

Chiral succinates can be prepared simply (e.g., via Stobbe condensation) from unsubstituted succinic esters and aldehydes or ketones, followed by asymmetric hydrogenation of the intermediate β-substituted itaconate derivatives. For example, itaconic acid or its sodium salt, can be enantioselectively hydrogenated to 2-methylsuccinic acid with rhodium catalysts bearing the chiral ligand N-acyl-3,3'-bis(diphenylphosphino)pyrrolidine (BPPM) in up to 92% enantiomeric excess (ee) [I. Ojima et al., *Chem. Lett.*, 1978, 567; I. Ojima et al., *Chem. Lett.*, 1978, 1145; K. Achiwa, *Tetrahedron Lett.*, 1978, 1475]. A rhodium catalyst bearing the chiral diphosphine DIPAMP affords 2-methylsuccinate in up to 88% ee [W. C. Christofel, B. D. Vineyard, *J. Am. Chem. Soc.* 1979, 101, 4406; and U.S. Pat. No. 4,939,288]. Similar results have been obtained with a ruthenium catalyst containing the chiral diphosphine ligand BINAP [H. Kawano et al., *Tetrahedron Lett.*, 1987, 28, 1905]. Rhodium catalysts bearing modified DIOP ligands provide 2-methylsuccinic acid derivatives with variable enantioselectivities, between 7 and 91% ee. In these latter reactions, the ee value is very dependent on the rhodium catalyst precursor and whether the free acid or the ester is used [T. Morimoto et al., *Tetrahedron Lett.*, 1989, 30, 735]. Better results have been reported with a neutral rhodium catalyst of the chiral diphosphine 2,2'-bis(dicyclohexylphosphino)-6,6'-dimethyl-1,1'-biphenyl (BICHEP), whereby dimethylitaconate was hydrogenated in 99% ee [T. Chiba et al., *Tetrahedron Lett.*, 1991, 32, 4745].

In contrast to the success achieved with unsubstituted itaconate derivatives, asymmetric hydrogenation of β-substituted itaconic acid derivatives has been more challenging; relatively few reports of high enantioselectivity (over 90% ee) have appeared. No enantioselectivities above 90% ee have been reported for β-alkyl-substituted itaconates.

Itaconate derivatives that possess two substituents in the β-position (β,β-disubstituted itaconates of formula 1 where $R^3, R^4 \neq H$) have thus far proven impossible to hydrogenate with high enantioselectivities and high rates. The only reported example of this type revealed that dimethyl β,β-dimethylitaconate may be hydrogenated with a Rh-TRAP catalyst system with the highest enantioselectivities being 78% ee [R. Kuwano et al, *Tetrahedron: Asymmetry*, 1995, 6, 2521].

It should be noted that enantiomerically pure compounds are required for many applications in, for example, the pharmaceutical industry. Consequently, providing enantiomeric purity is the ultimate objective of an asymmetric process, and achieving high enantioselectivity in a transformation of the type described herein is crucial from a process standpoint. 90% ee is often selected as a lower acceptable limit because compounds often may be purified to enantiomeric purity through recrystallisation when the initial value is above 90% ee. Enantiomeric excesses lower than 90% ee become increasingly more difficult to purify.

SUMMARY OF THE INVENTION

The present invention is based on the discovery that an efficient and high-yielding preparation of an enantiomerically enriched chiral carboxylic acid by asymmetric hydrogenation, e.g. in the presence of a transition metal complex of a chiral phosphine, is facilitated by use of particular salt forms of the hydrogenation substrate. Examples of such substrates are itaconates, which are referred to herein by way of example only. More generally, the products of the invention have the partial formula C—C—C—COOX, X being a cation. The corresponding acid will usually be obtained, on work-up.

The use of salt forms can have a number of advantages. Firstly, formation and isolation of a salt form, using a substantially stoichiometric amount of base, may provide a convenient means of effecting substrate purification prior to hydrogenation, should this be required. Secondly, at a given molar ratio of substrate to catalyst (S/C ratio) and reaction time, a higher substrate conversion and/or higher enantioselectivity can be achieved. Thirdly, high reaction rates allow reactions to be performed at low temperatures, e.g. 0° C., whereby higher product enantiopurity is observed.

DESCRIPTION OF THE INVENTION

The substrate for hydrogenation is prochiral, i.e. it is asymmetrically substituted about the C=C bond. One substituent is —C—COOX, and the combination of chain length and carboxylate anion provides the ability of the substrate to coordinate a metal catalyst. There may be none or any substituents on the same C atom of the C=C bond as —C—COOX, provided that they do not interfere with the reaction. For example, in the hydrogenation of a substrate of the formula $R^3R^4C=CR^1—CH_2—COOR^2$, $R^1$, $R^3$ and $R^4$ are each essentially spectators, although $R^3$ and $R^4$ are not both hydrogen. A characteristic of this invention is that no carboxylate function other than COOX is necessary.

Such substrates are known or may be prepared by methods known to those skilled in the art. In the particular case when $R^1$ is $COOR^2$, COOalkyl or COOaryl, both β-substituted and β,β-disubstituted derivatives may be prepared. Itaconates for use as substrates are also described in PCT/GB98/03784 and U.S. patent application Ser. No. 09/213,745, filed Dec. 17, 1998, the contents of which are incorporated herein by reference.

Suitable substrates for the hydrogenation process outlined above are of the general structure 7 or 8 (for the preparation of products 2)

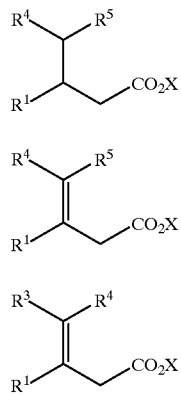

or a mixture thereof, wherein $R^1$, $R^3$ and $R^4$ can be independently H or an organic group of up to 30 C atoms or $R^3$ and $R^4$ are joined to form a ring, provided that at least one of $R^3$ and $R^4$ is not H. In one embodiment, the invention provides an improved procedure in the case where one of $R^3$ and $R^4$ is H; typically, the other is $C_{1-20}$ alkyl or aralkyl. By way of example, the fact that β,β-disubstituted itaconates can be effectively hydrogenated in this process means also that $R^3$ and $R^4$ may each be an organic group of up to 30 C atoms, e.g. $C_{1-20}$ alkyl or aralkyl, and preferably the same, or may be linked to form a ring, e.g. a saturated carbocyclic ring. In this case, $R^1$ may be $COOC_{1-10}$ alkyl, COO aryl or COO aralkyl.

X may represent a metal, e.g. alkali metal, or other cation. The metal salt may be preformed or formed in situ, by introducing a strong base such as a metal alkoxide, e.g. NaOMe.

Alternatively, the salt may be formed with, for example, a counterion $YH^+$ such as that derived from an amine Y or a phosphine Y. Primary $C_{1-10}$ alkylamines and cycloalkylamines are preferred, in particular, tert-butylamine. Tertiary amines such as triethylamine may also be used.

Especially when an amine or phosphine salt is used, it is usually isolated prior to use in the process, but alternatively may be generated in situ. Isolation of the precursor salt can be advantageous as a means of effecting substrate purification, usually by crystallisation, e.g. to remove any regioisomeric contaminants. However, this step is not always necessary, especially when the Stobbe condensation is carried out under carefully controlled conditions where regioisomeric contaminants are not formed, e.g. at a temperature of around 5° C. rather than at normal room temperature.

Temperature effects may also be noted in the process of the present invention, with a lowering of reaction temperature resulting in improved enantioselectivities for certain substrates, e.g. when $R^3/R^4$ is a cyclic group, or if the precursor is an amine or phosphine salt. Especially in such cases, the reaction temperature may be less than 10° C., and is preferably −25 to +5° C.

Catalysts that are suitable for the asymmetric hydrogenation process comprise a transition metal complexed to an appropriate chiral phosphine ligand. Preferably, the ligand is a monophosphine or diphosphine ligand which may be used in either enantiomeric form. The preferred transition metal is rhodium; others that may be used include ruthenium and iridium.

Preferred phosphines are those incorporating an appropriately substituted phosphorus heterocycle of general structure 10, where n is zero or an integer 1 to 6, and where the carbocyclic framework of 10 is substituted with one or more R substituents such that the structure 10 is a chiral entity, and where the R substituent is an organic group of up to 20 C atoms, typically a $C_{1-10}$ linear or branched hydrocarbon substituent, but which also may contain heteroatoms. In the case where more than one R substituent is present in the structure 10, these R substituents may be the same or different, and may be joined to form ring systems fused with the parent carbocyclic framework illustrated for 10. Monophosphines containing the phosphorus heterocyclic unit 10 take the general structure 11, where R' is an organic group of up to 20 C atoms. Alternatively, two phosphorus heterocycles of structure 10 may be tethered with a linking unit to form a diphosphine of general structure 12, where the linking unit is an organic group of up to 30 C atoms, linear, branched or cyclic, hydrocarbon or heteroatomic in nature.

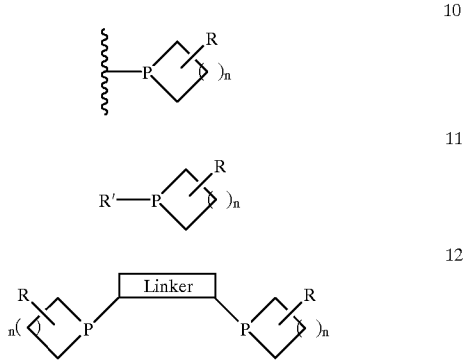

Examples of these ligands encompass 2,4-disubstituted phosphetanes 13, e.g. as disclosed in WO-A-9802445, as well as the DuPHO [U.S. Pat. No. 5,171,892] and BPE [U.S. Pat. No. 5,008,547] series of bisphospholanes, 14 and 15, respectively. The latter ligands constitute the most preferred class of disphosphines for the asymmetric hydrogenation process described herein.

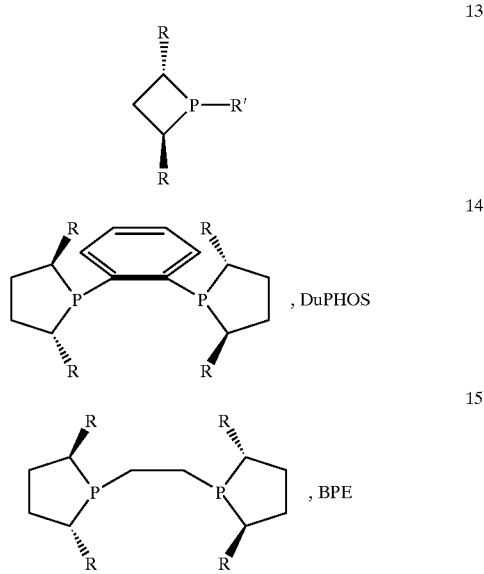

The possession of a series of homologous ligands of types 11–15 which are substituted with a range of different R groups is crucial for success in asymmetric hydrogenations since it is difficult to predict which catalyst will hydrogenate a particular substrate type with high selectivity. For a given substrate, enantioselectivities may be dependent upon the nature of the R-substituent attached to the carbocyclic ring of the DuPHOS, BPE or other ligand (as can be seen from Table 1, below). Typically, a range of ligand-metal complexes may be screened, in order to identify the optimum catalyst for a given transformation, although such screening is readily done by one of ordinary skill in the art, if necessary with reference to the guidance provided herein. The appropriate complex may change, from substrate type to substrate type: rhodium complexes containing certain DuPHOS and BPE ligands have been shown to hydrogenate several types of olefinic substrates, such as enamides, with very high enantioselectivity [Burk et al., *J. Am. Chem. Soc.,* 1993, 115, 10125], while other substrates such as α,β-unsaturated carboxylic acids and allylic alcohols are reduced with only very low selectivities. For example, both β-substituted and β,β-disubstituted α-enamide esters may be hydrogenated to α-amino acid derivatives with high enantioselectivity using certain DuPHOS and BPE-rhodium catalysts [Burk et al., *J. Am. Chem. Soc.,* 1995, 117, 9375]. Furthermore, β-substituted α-arylenamides may be hydrogenated to α-arylalkylamine derivatives with high enantioselectivities [Burk et al., *J. Am. Chem. Soc.,* 1996, 118, 5142], yet β,β-disubstituted α-arylenamides are hydrogenated with the same catalysts with very low enantioselectivity (0–5% ee).

The value of using a salt as the substrate is evident in the case where the hydrogenation substrate is a β,β-disubstituted itaconate derivative, for example wherein $R^3 = R^4 =$ methyl. Otherwise, it may be that high substrate conversion is difficult to achieve at acceptable S/C ratios (typically >200:1). See, for example, Examples 1 and 2. In the former, hydrogenation of the tert-butylamine salt of 2-isopropylidenesuccinic acid 1-methyl ester, catalysed by a rhodium(I) complex of (R,R)-methyl BPE, with S/C=500:1, was conducted at 0° C. using methanol as solvent. This gave complete substrate conversion after 20 hours, to afford after said cracking (R)-2-isopropylsuccinic acid 1-methyl ester in 95% ee. Enrichment of the salt to at least 99% ee could then be simply achieved by reslurrying in fresh solvent and then filtering. In Example 2, reaction of the free acid of of 2-isopropylidenesuccinic acid 1-methyl ester under similar conditions, with a higher catalyst loading (S/C=300:1), gave only 33% substrate conversion, with (R)-2-isopropylsuccinic acid 1-methyl ester produced in 88% ee.

Overall, the present invention provides a straightforward process for the synthesis of valuable, highly enantiomerically enriched chiral carboxylic acid derivatives, starting from readily available, inexpensive starting materials.

The following Examples illustrate the invention, except Example 2 which is comparative.

TBME=tert-butyl methyl ether

GC=gas chromatographic analysis

EXAMPLE 1

A. A solution of tert-butylamine (124 mL, 1.19 mmol) in tert-butyl methyl ether (TBME; 100 mL) was added dropwise, at room temperature, over a period of 2 hours, to a solution of 2-isopropylidenesuccinic acid 1-methyl ester (205 g, 1.19 mmol) in TBME (350 mL). The resulting thick suspension was stirred at room temperature for an additional hour, then the solid precipitate was collected, washed with TBME (1 L) and dried under vacuum at 40° C. for 48 hours to give 181 g of the salt as a white powder (yield: 62%).

B. A solution of the tert-butylamine salt of 2-isopropylidenesuccinic acid 1-methyl ester (162 g, 0.66 mol) in methanol (800 mL) was transferred to a 2 L high pressure hydrogenation vessel and degassed by pressurizing and venting four times with 10 bar of hydrogen. The vessel was then cooled to 0° C. and a solution of [Rh(COD)(S,S)-Me-BPE]OTf (0.80 g, 0.0013 mmol) in methanol (10 mL) was added through the solvent port. The reaction was purged again with hydrogen and stirred at 0° C. under a pressure of hydrogen of 10–7 bar. After 22 hours, the temperature was allowed to raise to room temperature, the vessel was vented in a fume hood, the reaction mixture was transferred to a round-bottomed flask and the solvent was evaporated under reduced pressure. A sample (1 g) of the resulting solid residue was partitioned between HCl 2N (5 mL) and ethyl acetate (5 mL). The organic layer was dried over $MgSO_4$ and evaporated to give 2-(S)-isopropylsuccinic acid 1-methyl ester, ee 96% by GC. The bulk residue was suspended in ethyl acetate (600 mL) and stirred at room temperature for 48 hours, then collected and dried under vacuum to give 154 g of the tert-butylamine salt of 2-(S)-isopropylsuccinic acid monomethyl ester (yield: 94%). A sample (1 g) of the salt was worked up and analyzed as above, indicating an enantiomeric excess of 99% for the free acid.

EXAMPLE 2 (COMPARATIVE)

2-Isopropylidenesuccinic acid 1-methyl ester (0.86 g, 5.0 mmol) and sodium methoxide (0.10 g, 1.8 mmol) were placed in a 60 mL high pressure hydrogenation vessel and the vessel was purged with hydrogen (by pressurizing and venting three times with 10 bar of hydrogen). Methanol (9 mL, previously degassed by bubbling nitrogen for one hour at room temperature under stirring) was added through the solvent port and the vessel was then cooled to 0° C. A solution of [Rh(COD)(R,R)Me-BPE]OTf (0.010 g, 0.016 mmol, substrate/catalyst: 300/1) in methanol (1 mL) was added and the reactor was charged with 10 bar of hydrogen. The reaction was stirred at 0° C. for 20 hours, then the solvent was evaporated under reduced pressure and the residue was partitioned between HCl 2N (20 mL) and ethyl acetate (20 mL). The organic layer was separated, dried over $MgSO_4$, evaporated to give a pale yellow oil. $^1H$ NMR analysis of the crude indicated that the reduced product and the starting material were present in a ratio 33:67. The enantiomeric excess of 2-(R)-isopropylsuccinic acid 1-methyl ester was 88% by GC. This result shows that, for this particular substrate, the salt form used in Example 1 is preferable.

EXAMPLE 3

The tert-butyl ammonium salt of 2-isopropylidenesuccinic acid 1-methyl ester (0.80 g, 3.3 mmol) was prepared, and placed in a 60 mL high pressure hydrogenation vessel and the vessel was purged with hydrogen (by pressurizing and venting three times with 10 bar of hydrogen). Methanol (9 mL, previously degassed by bubbling nitrogen for one hour at room temperature under stirring) was added through the solvent port and the vessel was then cooled to 0° C. A solution of [Rh(COD)(R,R)Me-BPE]OTf (0.004 g, 0.0065 mmol), substrate/catalyst, 500/1) in methanol (1 mL) was added and the reactor was charged with 10 bar of hydrogen. The reaction was stirred at 0° C. for 20 hours, then the solvent was evaporated under reduced pressure and the residue was partitioned between HCl 2N (20 mL) and ethyl acetate (20 mL). The organic layer was separated, dried over $MgSO_4$, evaporated to give a pale yellow oil. $^1H$ NMR analysis of the crude indicated that the conversion to the reduction product was more than 95%. The enantiomeric excess of 2-(R)-isopropylsuccinic acid 1-methyl ester was 95% by GC.

EXAMPLE 4

The tert-butylamine salt of (E)-2-(3-phenyl-2-propenylidene)succinic acid 1-methyl ester (1 g, 4.1 mmol) was prepared. This salt and [Rh(COD)(R,R)Me-DuPhos]BF$_4$ (6 mg, 0.01 mmol, substrate/catalyst: 400:1) were weighed in a 60 mL high pressure hydrogenation vessel and an atmosphere of nitrogen was introduced by evacuating the reactor and refilling with oxygen-free dry nitrogen. This procedure was repeated three times. Methanol (5 mL, previously degassed by bubbling nitrogen for one hour at room temperature while stirring) was added to the reactor through the solvent port. The reactor was charged with 690 kPa (100 psi) of hydrogen and the pressure released. The reactor was then repressurised to 965 kPa (140 psi) and the reaction was stirred for 16 hours, then the solvent was evaporate under reduced pressure and the residue was partitioned between HCl 2N (20 mL) and ethyl acetate (20 mL). The organic layer was separated, dried over MgSO$_4$, evaporated to give a pale yellow oil. $^1$H NMR analysis of the crude indicated that the conversion to the reduction product was complete. The enantiomeric excess of 2-(S)-(3-phenyl-2-propenyl)succinic acid 1-methyl ester was 99% by GC.

EXAMPLE 5

The tert-butylamine salt of 2-cyclohexylidenesuccinic acid 1-methyl ester (0.91 g, 3.2 mmol) was prepared, and placed in a 60 mL high pressure hydrogenation vessel. The vessel was purged with hydrogen (by pressurizing and venting three times with 10 bar of hydrogen). Methanol (9 mL, previously degassed by bubbling nitrogen for one hour at room temperature under stirring) was added through the solvent port and the vessel was then cooled to 0° C. A solution of [Rh(COD)(R,R)Me-BPE]OTf (0.004 g, 0.0065 mmol, substrate/catalyst: 500/1) in methanol (1 mL) was added and the reactor was charged with 10 bar of hydrogen. The reaction was stirred at 0° C. for 20 hours, then the solvent was evaporated under reduced pressure and the residue was partitioned between HCl 2N (20 mL) and ethyl acetate (20 mL). The organic layer was separated, dried over MgSO$_4$, evaporated to give 0.75 g of 2-cyclohexylsuccinic acid monomethyl ester as a pale yellow oil (yield 82%). The enantiomeric excess of 2-(R)-cyclohexylsuccinic acid 1-methyl ester was 96% by GC.

EXAMPLE 6

The tert-butylamine salt of 2-(2-adamantylidene)succinic acid 1-methyl ester (0.54 g, 1.6 mmol) was prepared, and placed in a 60 mL high pressure hydrogenation vessel. The vessel was purged with hydrogen (by pressurizing and venting three times with 10 bar of hydrogen). Methanol (9 mL, previously degassed by bubbling nitrogen for one hour at room temperature under stirring) was added through the solvent port and the vessel was then cooled to 0° C. A solution of [Rh(COD)(R,R)Me-BPE]Otf (0.004 g, 0.0065 mmol, substrate/catalyst: ~250/1) in methanol (1 mL) was added and the reactor was charged with 10 bar of hydrogen. The reaction was stirred at 0° C. for 23 hours, then the solvent was evaporated under reduced pressure and the residue was partitioned between HCl 2N (20 mL) and ethyl acetate (20 mL). The organic layer was separated, dried over MgSO$_4$, evaporated to give a pale yellow oil. $^1$H NMR analysis of the crude indicated that the conversion to the reduction product was complete. The enantiomeric excess of 2-(R)-(2-adamantanyl)succinic acid monomethyl ester was 78% by GC. In similar experiments, carried out at room temperature (approx. 20° C.), 2-(R)-(2-adamantanyl)succinic acid monomethyl ester was obtained with 63% ee.

EXAMPLE 7

A. A solution of tert-butylamine (0.91 g, 12.4 mmol) in tert-butyl methyl ether (TBME: 2 mL) was added dropwise, at room temperature, to a solution of 3-phenyl-3-butenoic acid (1.87 g, 12.4 mmol) in TBME (8 mL). The resulting thick suspension was stirred at room temperature for 15 minutes, then the solid precipitate was collected and dried under vacuum to give the salt as a white powder (1.74 g, 63% yield).

B. The tert-butylamine salt of 3-phenyl-3-butenoic acid (0.22 g, 1 mmol) was placed in a 60 mL high pressure hydrogenation vessel and the vessel was purged with hydrogen (by pressurising and venting three times with 10 bar of hydrogen). Methanol (8 mL, previously degassed by bubbling nitrogen for one hour at room temperature under stirring) was added through the injection port and the vessel was cooled to 0° C. A solution of [Rh(COD)/(S,S)Me-BPE]OTf (0.006 g, 0.01 mmol, substrate/catalyst: 100/1) in methanol (2 mL) was added and the reactor was charged with 7 bar of hydrogen. The reaction was stirred at 0° C. for 14 hours, then the solvent was evaporated under reduced pressure. $^1$H NMR analysis of the crude indicated that the conversion to the reduction product was quantitative. The crude was then partitioned between HCl 2N (40 mL) and dichloromethane (40 mL). The organic layer was separated, dried over MgSO$_4$, evaporated to give a pale yellow oil (0.13 g, 87% yield). The enantiomeric excess of (R)-3-phenylbutanoic acid was determined by chiral HPLC analysis to be 69%. In a similar experiment carried out at room temperature (approx 20° C.). (R)-3-phenylbutanoic acid was obtained with 62% ee.

EXAMPLE 8

A. The same procedure as Example 7A was used to produce the tert-butylamine salt of 3,4-diphenyl-3-butenoic acid (66% yield) as a mixture of two geometric isomers in a 4:1 ratio (as determined by $^1$H NMR analysis).

B. The tert-butylamine salt of 3,4-diphenyl-3-butenoic acid (0.31 g, 1 mmol, mixture of E/Z isomers) and [Rh(COD)(S,S)Me-BPE]OTf (6 mg, 0.01 mmol, substrate/catalyst: 100/1) were placed in a 60 mL high pressure hydrogenation vessel and the vessel was purged with hydrogen (by pressurising and venting three times with 10 bar of hydrogen). Methanol (10 mL, previously degassed by bubbling nitrogen for one hour at room temperature under stirring) was added through the injection port and the reactor was charged with 7 bar of hydrogen. The reaction was stirred at room temperature (approx 20° C.) for 14 hours, then the solvent was evaporated under reduced pressure. $^1$H NMR analysis of the crude indicated that the conversion to the reduction product was quantitative. The crude was then partitioned between HCl 2N (40 mL) and dichloromethane (40 mL). The organic layer was separated, dried over MgSO$_4$, evaporated to give a pale yellow oil (0.19 g, 83% yield). The enantiomeric excess of (R)-3,4-diphenylbutanoic acid was determined by chiral HPLC analysis to be 60%.

What is claimed is:

1. A process for the preparation of an enantiomerically enriched chiral carboxylic acid derivative of formula 2

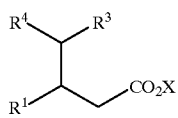

2 wherein $R^1$, $R^3$ and $R^4$ are each independently H or a non-interfering organic group of up to 30 C atoms, or any two are linked to form a ring, provided that $R^3$ and $R^4$ are not both H, which comprises formation of a dehydro precursor salt of formula 7

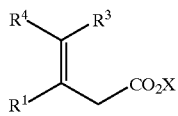

7 wherein X is a cation, optionally in the form of a mixture of such compounds when one of $R^3$ and $R^4$ is H, by reaction of a corresponding precursor acid with an at least substantially stoichiometric amount of base, and asymmetric hydrogenation of the salt in the presence of a transition metal complex comprising rhodium and a chiral phosphine ligand having the partial formula 10

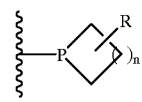

10 wherein n is 0 to 6 and R represents at least one non-hydrogen organic group of up to 30 C atoms.

2. The process according to claim 1, wherein $R^3$ and $R^4$ are each, or are linked to form, an organic group of up to 30 C atoms.

3. The process according to claim 2, wherein $R^3 = R^4$.

4. The process according to claim 1, wherein one of $R^3$ and $R^4$ is H.

5. The process according to claim 1, wherein $R^3$ and $R^4$ are independently selected from the group consisting of H, $C_{1-20}$ alkyl, aryl and aralkyl.

6. The process according to claim 1, wherein $R^1$ is $COOC_{1-10}$ alkyl or COOaralkyl.

7. The process according to claim 1, wherein the precursor is an amine or phosphine salt.

8. The process according to claim 7, wherein the precursor is an amine salt.

9. The process according to claim 8, wherein the amine is a primary amine.

10. The process according to claim 9, wherein the amine is tert-butylamine.

11. The process according to claim 8, wherein the amine is a tertiary amine.

12. The process according to claim 11, wherein the amine is triethylamine.

13. The process according to claim 1, wherein the precursor salt is a metal salt.

14. The process according to claim 13, wherein the metal is an alkali metal.

15. The process according to claim 14, wherein the metal is sodium or potassium.

16. The process according to claim 1, wherein the precursor salt is isolated prior to use in the asymmetric hydrogenation.

17. The process according to claim 1, wherein the precursor salt is generated in situ.

18. The process according to claim 1, wherein the ligand is of formula 11 or 12

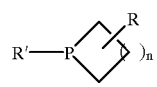

11

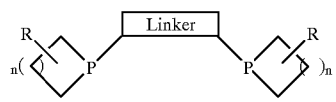

12 wherein Linker and R' are independently any non-hydrogen organic group of up to 30 C atoms.

19. The process according to claim 18, wherein the ligand is of formula 14 or 15

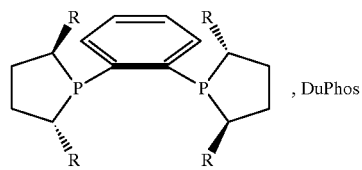

14

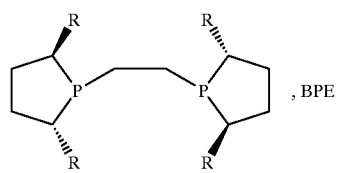

15 and wherein R is a $C_{1-8}$ linear or branched alkyl group or an aromatic group.

20. The process according to claim 1, wherein the reaction temperature is less than 10° C.

21. The process according to claim 1, which gives the product in an enantiomeric excess of at least 90%.

22. The process according to claim 1, wherein $R^3$ and $R^4$ are linked to form a ring.

* * * * *